(12) United States Patent
Hsing et al.

(10) Patent No.: US 9,314,504 B2
(45) Date of Patent: Apr. 19, 2016

(54) USE OF MEMBERS OF IL-10 CYTOKINE FAMILY

(71) Applicants: Taipei Medical University, Taipei (TW); CHI MEI MEDICAL CENTER, Tainan (TW)

(72) Inventors: Ching-Hsi Hsing, Taipei (TW); Ching Hua Yeh, Tainan (TW); Li-Yun Wang, Tainan (TW); Ding Ping Sun, Tainan (TW)

(73) Assignees: TAIPEI MEDICAL UNIVERSITY, Taipei (TW); CHI MEI MEDICAL CENTER, Tainan (TW)

( * ) Notice: Subject to any disclaimer, the term of this patent is extended or adjusted under 35 U.S.C. 154(b) by 0 days.

(21) Appl. No.: 13/831,262

(22) Filed: Mar. 14, 2013

(65) Prior Publication Data

US 2014/0271539 A1    Sep. 18, 2014

(51) Int. Cl.
*A61K 38/20*    (2006.01)
*C07K 14/54*    (2006.01)

(52) U.S. Cl.
CPC .................................. *A61K 38/2066* (2013.01)

(58) Field of Classification Search
USPC .......................................... 514/9.4; 424/85.2
See application file for complete search history.

(56) References Cited

U.S. PATENT DOCUMENTS

| | | | |
|---|---|---|---|
| 7,309,687 B1 * | 12/2007 | Brines et al. ................... | 514/7.7 |
| 2003/0103941 A1 * | 6/2003 | Crombleholme et al. ... | 424/93.2 |
| 2003/0180892 A1 * | 9/2003 | Ebner et al. ................ | 435/69.52 |
| 2006/0188476 A1 * | 8/2006 | Olsen et al. .................. | 424/85.2 |
| 2009/0220450 A1 * | 9/2009 | Green et al. ................. | 424/85.2 |
| 2011/0280828 A1 * | 11/2011 | Abbas et al. ................ | 424/85.2 |

OTHER PUBLICATIONS

Sun et al. Interleukin (IL)-19 promoted skin wound healing by increasing fibroblast keratinocyte growth factor expression. Cytokine vol. 62:360-368 (Apr. 2013).*
Sa et al. The Effects of IL-20 Subfamily Cytokines on Reconstituted Human Epidermis Suggest Potential Roles in Cutaneous Innate Defense and Pathogenic Adaptive Immunity in Psoriasis. The Journal of Immunology, vol. 178: 2229-2240 (2007).*
Boniface. IL-22 inhibits epidermal differentiation and induces proinflammatory gene expression and migration of human keratinocytes. Journal of Immunology vol. 174:3695-3702 (2005).*
Phillips, A., The challenges of gene therapy and DNA delivery. J Pharm. Pharmacology 53: 1169-1174 (2001).*

* cited by examiner

*Primary Examiner* — Elizabeth C Kemmerer
*Assistant Examiner* — Regina M Deberry
(74) *Attorney, Agent, or Firm* — Muncy, Geissler, Olds & Lowe, P.C.

(57) ABSTRACT

The invention relates to a novel use of the members of the IL-10 cytokine family in wound healing. Particularly, the invention relates to the use of the member of the IL-10 cytokine family in the promotion of the proliferation and the migration of keratinocyte cells in wound healing.

3 Claims, 11 Drawing Sheets even with IL-6 and TNF-α after cardiac surgery with a cardiopulmonary bypass (CPB) (Hsing C H, Hsieh M Y, Chen W Y, Cheung So E, Cheng B C, Chang M S. *Induction of interleukin*-19 *and interleukin*-22 *after cardiac surgery with cardiopulmonary bypass. The Annals of thoracic surgery.* 2006; 81: 2196-201). Acutely induced IL-19 in systemic inflammation may promote lung and tissue injury in mice undergoing endotoxic shock (Hsing C H, Chiu C J, Chang L Y, Hsu C C, Chang M S. *IL*-19 *is involved in the pathogenesis of endotoxic shock. Shock* 2008; 29:7-15). IL-19 also controls antigen-presenting cells in the lungs and airway responses to microbial products. It was recently reported that IL-19 receptor signaling downregulates antigen-specific T cell responses. IL-19 reduces T-cell responses and promotes the regulatory activity of CD4+ T cells. In patients undergoing coronary artery bypass grafting (CABG) with a CPB, induced IL-19 contributes to cell-mediated immunosuppression. IL-19 promotes breast cancer progression by inducing proinflammatory mediators. IL-19 has multiple functions in immune regulation and disease, and the immunomodulatory role of IL-19 is emerging in psoriasis and chronic inflammatory disorders in general. It has been previously shown that IL-19 expression was seen in basal and suprabasal keratinocytes in a continuous pattern, and was increased in psoriatic epidermis (Li H H, Lin Y C, Chen P J, Hsiao C H, Lee J Y, Chen W C, et al. *Interleukin*-19 *upregulates keratinocyte growth factor and is associated with psoriasis. Br J Dermatol.* 2005; 153:591-5). In addition, IL-19 upregulated the expression of KGF in CD8+ T cells (Li H H, Lin Y C, Chen P J, Hsiao C H, Lee J Y, Chen W C, et al. *Interleukin*-19 *upregulates keratinocyte growth factor and is associated with psoriasis. Br J Dermatol.* 2005; 153:591-5), which suggested that IL-19 is involved in the proliferation of keratinocytes in psoriasis. However, Davis P A et al. concluded that CD8(+) lymphocytes downregulates wound healing (Davis P A, Corless D J, Aspinall R, Wastell C. *Effect of CD*4(+) *and CD*8(+) *cell depletion on wound healing. The British journal of surgery.* 2001; 88:298-304). Therefore, even if IL-19 upregulated the expression of KGF in CD8+ T, it cannot promote wound healing.

U.S. Pat. No. 5,045,887 relates to healing an external wound of a mammal by administering a composition containing purified platelet-derived growth factor and purified interleukin-1 or administering a composition containing purified insulin-like growth factor and interleukin-1. U.S. Pat. No. 5,202,118 provides wound healing compositions comprising IL-1-alpha and IL-1-beta. U.S. Pat. No. 6,001,357 provides a method of enhancing healing of a wound wherein said wound is caused by cutting, piercing, abrasion, surgical incision, ulceration, thermal burn, chemical burn, radiation burn or friction burn, comprising administering to a mammal in need thereof an amount of anti-IL-5 antibody into a wound site sufficient to result in healing of said wound.

Although there are prior art references disclosing relationship between the members of interleukin family and wound healing, none of them is relevant to the IL-10 cytokine family. The correlation of the IL-10 cytokine family with wound healing remains unclear.

SUMMARY OF THE INVENTION

The invention provides a method for promotion of the proliferation and/or increasing the migration of a keratinocyte cell in wound healing, comprising administering to the fibroblast cell an effective amount of one or more members of the IL-10 cytokine family. In one embodiment, members of the IL-10 cytokine family used in the invention include IL-10, IL-19, IL-20, IL-22, IL-24, IL-26, IL-28 and IL-29. More preferably, the member of the IL-10 cytokine family is IL-19 or IL-20. In another embodiment, members of the IL-10 cytokine family are for topical or parenteral administration. In a further embodiment, the wound healing is cutaneous wound healing or diabetes wound healing.

DETAILED DESCRIPTION OF THE INVENTION

Figure 1A:
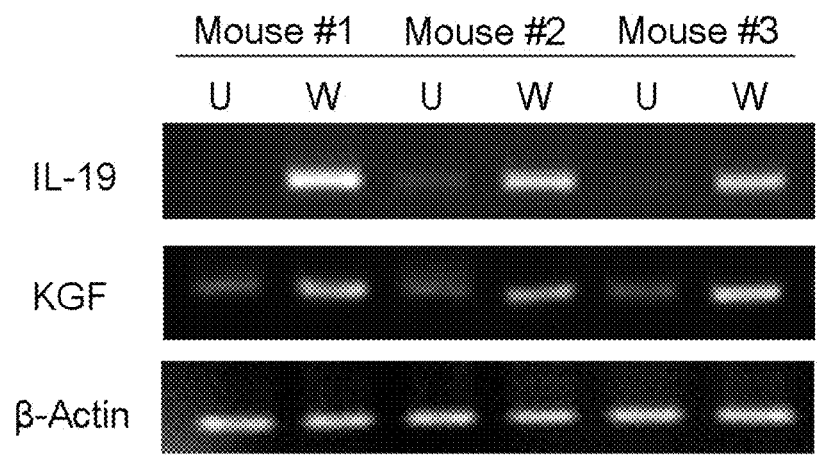
FIGS. 1A-1C show that IL-19 and KGF were upregulated during skin wound healing. (A) We used RT-PCR to determine the expression of IL-19 and KGF mRNA in three unwounded (U) and wounded (W) mouse skin tissue samples 24 h after the mouse skin had been injured. We used RT-qPCR to determine the (B) IL-19 and (C) KGF mRNA levels of wounded mouse skin. IL-19 increased 12 h and KGF increased 24 h after the skin had been wounded. Both increases declined 48 h and 72 h after the skin had been wounded. Data are means±SD, n=6 in each group, *P<0.05.

The invention surprisingly found that a member of the IL-10 cytokine family (preferably IL-19) promotes the proliferation of keratinocyte cell in wound healing; preferably, the IL-10 cytokine family indirectly promote the proliferation of keratinocyte. In addition, a member of the IL-10 cytokine family (preferably IL-19) significantly increases the migration of keratinocyte cells in wound healing. The invention also surprisingly found that a member of the IL-10 cytokine family (preferably IL-19) exhibits the above functions in a diabetic subject and can thus promote diabetes wound healing.

All scientific and technical terms used in this application have meanings commonly used in the art unless otherwise specified. As used in this application, the following words or phrases have the meanings specified.

The terms "a" and "an" refer to one or to more than one (i.e., to at least one) of the grammatical object of the article.

The term "expression" when used in the context of expression of a gene or nucleic acid refers to the conversion of the information contained in a gene into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include messenger RNAs which are modified by processes such as capping, polyadenylation, methylation, and editing, and proteins modified by, for example, methylation, acetylation, phosphorylation, ubiquitination. ADP-ribosylation, myristilation, and glycosylation.

The terms "promote," "promotion," and "promoting" refer to an increase in an activity, response, condition, disease or other biological parameter. The term "promoting wound healing" refers to augmenting, improving, increasing, or inducing closure, healing or repair of a wound.

The term "subject" includes living organisms such as humans, monkeys, cows, sheep, horses, pigs, cattle, goats, dogs, cats, mice, rats, cultured cells, and transgenic species thereof. In a preferred embodiment, the subject is a human.

The term "administering" includes routes of administration which allow the active ingredient of the invention to perform their intended function.

The term "treat" or "treatment" refers to a method of reducing the effects of a disease or condition. Treatment can also refer to a method of reducing the underlying cause of the disease or condition itself rather than just the symptoms. The treatment can be any reduction from native levels and can be, but is not limited to, the complete ablation of the disease, condition, or the symptoms of the disease or condition.

The term "effective amount" means an amount of an immunomodulatory protein effective to treat and/or prevent wound healing.

In one aspect, the invention provides a method for promotion of the proliferation and the migration of a keratinocyte cell in wound healing, comprising administering to the fibroblast cell an effective amount of one or more members of the IL-10 cytokine family. Preferably, the proliferation of a keratinocyte cell is indirectly promoted.

In one embodiment, the invention provides a method for promotion of the proliferation of keratinocyte cells in wound healing, comprising administering to the keratinocyte cell an effective amount of one or more members of the IL-10 cytokine family. Preferably, the proliferation of a keratinocyte cell is indirectly promoted.

In one embodiment, the invention provides a method for the increase of the migration of a keratinocyte cell in wound healing, comprising administering to the keratinocyte cell an effective amount of one or more members of the IL-10 cytokine family.

In one embodiment, members of the IL-10 cytokine family used in the invention include IL-10, IL-19, IL-20, IL-22, IL-24, IL-26, IL-28 and IL-29. More preferably, the member of the IL-10 cytokine family is IL-19 or IL-20.

A "therapeutically effective amount" of the member of the IL-10 cytokine family, as described above, refers to a sufficient amount of the member of the IL-10 cytokine family to promote the proliferation and the migration of a keratinocyte cell at a reasonable benefit/risk ratio applicable to any medical treatment. In one embodiment, an effective amount of the active ingredient is ordinarily supplied at a dosage level from 0.0001 µg/kg to about 50 µg/kg of body weight, especially from about 0.001 µg/kg to 5 µg/kg of body weight.

In one embodiment, the member of the IL-10 cytokine family is for topical or parenteral administration.

In one embodiment, the wound healing is cutaneous wound healing or diabetes wound healing.

The term "wound" and "tissue injury" can be used interchangeably. The wound can be an internal wound or an external wound found in any location of a subject. The wounds to be treated by the invention may include, but are not limited to, the following: surgical wounds; bites; burns, acid and alkali burns, cold burn (frostbite), sun burn; minor cuts; major cuts; abrasions; lacerations; wounds caused by gunshot or knife injury; wounds caused by congenital disorders; wounds following dental surgery; periodontal disease; wounds following trauma; tumor associated wounds, which can be classified as malignant cutaneous ulcers related to the primary tumor or metastases; ulcers, leg ulcers; foot ulcers; and pressure sores and corneal wounds. For example, the method of the invention may be used to treat an injury which causes epidermal damage such as incisions, wounds in which the skin is broken by a cutting instrument, and lacerations, wounds by which the skin is broken by a blunt or dull instrument, and wounds of the skin caused by friction. The method of the invention may also be used to treat dermatological disorders such as burns, Candidiasis and diaper rash, donor and receptor site wounds for skin transplants, ulcers (cutaneous, decubitus, venous stasis, sickle cell, and diabetic), psoriasis, skin rashes, and sunburn photo reactive process, and second and third degree burns. The method of the invention may also be used to protect or accelerate the healing of oral tissue such as mouth sores, surgical sites, and ulcerations. The method of the invention may also be used to treat wounds such as those which result from corneal ulcers, radial keratotomy, corneal transplants, epikaratophakia and other surgically induced wounds in the eye. In a preferred embodiment, the method of the invention is used to treat wounds such as contusion, incisions and lacerations.

The method of the invention may also be used to treat an internal organ wound of a subject. In addition, the method of the invention may also be used to treat oxidative damage during transport and transplantation due to reperfusion injury following ischemia. The method of the invention may be used to abrogate reperfusion injury to such transplant organs as well as resuscitate and cause proliferation of cells.

The active ingredient of the invention (i.e., the member of the IL-10 cytokine family used in the invention) may be formulated as various compositions and administered in a number of ways depending on whether local or systemic treatment is desired, and on the area to be treated. Administration may be topically (including ophthalmically, vaginally, rectally, intranasally), or parenterally (for example by intravenous drip, subcutaneous, intraperitoneal or intramuscular injection). Multiple doses can also be administered. It will be understood, however, that the total daily usage of the active ingredients and compositions of the present invention will be decided by the attending physician within the scope of sound medical judgment. The specific therapeutically effective dose level for any particular patient will depend upon a variety of factors, including the disorder being treated and the severity of the disorder, activity of the specific compound employed; the specific composition employed; the age; body weight; general health; sex and diet of the patient; the time of administration; route of administration; rate of excretion of the specific compound employed; the duration of the treatment; drugs used in combination or coincidental with the specific drug employed; and like factors well-known in the medical arts. For example, it is well within the skill of the art to start doses of the active ingredient at levels lower than those required to achieve the desired therapeutic effect and to gradually increase the dosage until the desired effect is achieved.

By way of an example, the active ingredient has been formulated in a simple delivery vehicle. However, the active ingredient may be lyophilized or incorporated in a gel, cream, biomaterial or sustained release delivery vehicle.

The active ingredient will generally be combined with a pharmaceutically acceptable carrier. The term "pharmaceutically acceptable carrier" refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids and amino acid copolymers. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles.

The active ingredient may also be provided in the form of a wound dressing. That is to say, the active ingredient is provided in the form of a liquid, semi-solid or solid composition for application directly to the surface of a wound, or the composition is applied to the surface of, or incorporated into, a solid wound contacting layer such as a wound dressing gauze or film. The wound dressing composition may be provided in the form of a fluid or a gel. The active ingredient may be provided in combination with conventional pharmaceutical excipients for topical application to a wound. Suitable carriers include: Hydrogels containing cellulose derivatives, including hydroxyethyl cellulose, hydroxymethyl cellulose, carboxymethyl cellulose, hydroxypropylmethyl cellulose and mixtures thereof, and hydrogels containing polyacrylic acid (Carbopols). Suitable carriers also include creams/ointments used for topical pharmaceutical preparations. In one embodiment of the invention, the wound dressing composition may be a slow release solid composition, in which the active ingredient of the invention is dispersed in a slow release solid matrix such as a matrix of alginate, collagen, or a synthetic bioabsorbable polymer.

In addition to the active ingredient of the invention formulated for parenteral administration, such as intravenous or intramuscular injection, other pharmaceutically acceptable forms may be performed.

Optionally, one or more other conventional wound healing agents (e.g. growth factors, peptides, proteolytic inhibitors, extracellular matrix components, fragments and peptides, steroids, cytokines, oxygen donators or vitamins) may also be used in the manufacture of the medicament and compositions according to the invention. Such conventional wound healing agents may also be used in the method of the present invention. The inclusion of these agents may allow a synergistic effect on wound healing. Such additional wound healing agent(s) may be administered separately, simultaneously or sequentially with the active ingredient of the invention. Thus, in one embodiment an effective dose of the active ingredient may be delivered in conjunction with or alternating with another effective wound healing agents from the following groups: growth factors, peptides, proteolytic inhibitors, extracellular matrix components, fragments and peptides, steroids, cytokines, oxygen donators and vitamins. In one embodiment, the patient may be administered the active ingredient of the invention and the additional wound healing agent(s) by means of a single medicament which comprises both the active ingredient of the invention and the additional wound healing agent(s). In another embodiment, the patient is administered the active ingredient of the invention and the additional wound healing agent(s) separately.

The members of IL-10 family (such as IL-19 and IL-20) can promote wound healing. Particularly, topically applied IL-19 and IL-20 promote cutaneous wound healing.

It will be understood that the invention has been described by way of example only and modifications may be made whilst remaining within the scope and spirit of the invention.

Example

Materials and Methods

Cell Lines

Human keratinocyte (HaCaT) and fibroblast (CCD966SK) cell lines were purchased from the American Type Culture Collection (Manassas, Va.). HaCaT cells were cultured in Dulbecco's Modified Eagle's Medium (DMEM) with 10% fetal bovine serum (FBS) (Life Technologies, Rockville, Md.), 100 µg/mL of streptomycin, and 100 units/mL of penicillin (HyClone, Thermo Scientific, Rockford, Ill.). CCD966SK cells were cultured in Minimum Essential Medium Eagle medium (MEM) (HyClone) and supplemented with 10% FBS, 100 µg/mL of streptomycin, and 100 units/mL of penicillin, 1% sodium pyruvate (HyClone) and 1% Non-Essential Amino Acid (GIBCO, Invitrogen, Carlsbad, Calif.). Cells were maintained in a humidified 5% $CO_2$ atmosphere at 37° C.

Animals and Wound Healing Model

BALB/c mice were from the National Cheng Kung University Laboratory Animal Center and cared for according to the guidelines set up by the National Science Council, Taiwan. The experimental protocol adhered to the rules of the Animal Protection Act of Taiwan and was approved by the Institutional Animal Care and Use Committee of Chi-Mei Medical Center. The mice were housed in a temperature— (25±1° C.) and humidity-controlled (60±5%) room and kept on a 12:12-hour light-dark cycle. All cage accessories were sterilized and autoclaved before being placed in the cage. The mice were fed standard laboratory chow and water ad libitum in the Laboratory Animal Center of Chi-Mei Medical Center.

The mice were anesthetized with isoflurane, wiped with 70% ethanol, and shaved. Once the skin was exposed, two full-thickness (including the panniculus carnosus) circular wounds (4 mm in diameter) on each mouse were created using a disposable biopsy punch. Each wound was photographed every day and analyzed using ImageJ software. The wounded skin together with a margin of healthy skin was excised using a biopsy punch (8 mm in diameter) at 12, 24, 48 and 72 h after injury for further analysis. In another experiment, mice were wounded as described above and topically treated with PBS, vehicle, IL-19 (400 ng/mL), or IL-20 (400 ng/mL) (n=6 in each group) twice daily. IL-19 was prepared in an ointment base (vehicle) formulated with 80% Vaseline and 20% liquid paraffin (Kwon Y B, Kim H W, Roh D H, Yoon S Y, Baek R M Kim J Y, et al. *Topical application of epidermal growth factor accelerates wound healing by myofibroblast proliferation and collagen synthesis in rat. Journal of veterinary science*. 2006; 7:105-9). The percentage of wound healing was measured every day for 7 days.

Reverse Transcriptase-Polymerase Chain Reaction (RT-PCR)

Total RNA was extracted using a reagent (RNA-Bee; Tel-Test, Friendswood, Tex.), and then the total RNA underwent reverse transcription as described in prior art reference (Hsing C H, Hsieh M Y, Chen W Y, Cheung So E, Cheng B C, Chang M S. *Induction of interleukin-19 and interleukin-22 after cardiac surgery with cardiopulmonary bypass. The Annals of thoracic surgery.* 2006; 81:2196-201). IL-19 and KGF mRNA were amplified using PCR with gene-specific primers (Table 1). PCR products were visualized on 2% agarose gels containing ethidium bromide. β-Actin amplification was used as an internal control. The relative quantity of PCR products is expressed as a fold increase relative to untreated controls.

Real Time Quantitative PCR Analysis

Real time quantitative PCR was done using the LightCycler-Fast Start DNA Master SYBR Green I kit (Roche, Indianapolis, Ind.). IL-19 and KGF mRNA were amplified using PCR with gene-specific primers (Table 1).

TABLE 1

Primer pairs used in this study

| Factor | Primer sequence (5'-3') Forward | Reverse |
|---|---|---|
| β-actin | GCTGGAAGGTGGACAGCGAG (SEQ ID NO: 1) | TGGCATCGTGATGGACTCCG (SEQ ID NO: 2) |
| hIL-19 | GGCAATGTCAGGAACAGAGG (SEQ ID NO: 3) | AGCGGAATAAGACAGCCTGA (SEQ ID NO: 4) |
| mIL-19 | TTCCACGAGATCAAGAGAGC (SEQ ID NO: 5) | CCTCCAGCTGATTGTAGTTG (SEQ ID NO: 6) |
| hKGF | AAGGCTCAAGTTGCACCAGG CAG (SEQ ID NO: 7) | GTGTGTCGCTCAGGGCTGGA AC (SEQ ID NO: 8) |
| mKGF | TGAGTCCGGAGCAAACGGCT (SEQ ID NO: 9) | CCTCAGGTACCACTGGGTGC GA (SEQ ID NO: 10) | m: mouse; h: human; m: mouse; IL: interleukin; KGF: keratinocyte growth factor.

Enzyme-Linked Immunosorbent Assay (ELISA)

Cell culture supernatants were collected and the levels of KGF were measured using ELISA kits (R&D Systems, Minneapolis, Minn.) according to the manufacturer's instructions. Concentrations of IL-19 were determined using ELISA with pairs of specific monoclonal or polyclonal antibodies described in prior art references (Hsing C H, Hsu C C, Chen W Y, Chang L Y, Hwang J C, Chang M S. *Expression of IL-19 correlates with Th2 cytokines in uraemic patients. Nephrol Dial Transplant.* 2007; 22:2230-8; Liao S C, Cheng Y C, Wang Y C, Wang C W, Yang S M, Yu C K, et al. *IL-19 induced Th2 cytokines and was up-regulated in asthma patients. J Immunol.* 2004; 173:6712-8). Results are expressed as the means of duplicate assays.

Cell Proliferation Assay

To determine the effect of IL-19 or KGF on keratinocyte proliferation, HaCaT cells were serum-starved for 24 hours and then exposed to various concentrations of IL-19 or KGF, as indicated, for 24 h. Cell proliferation was assessed using BrdU incorporation (BrdU ELISA colorimetric assay; Roche, Indianapolis, Ind.). To inhibit the effect of KGF, an antigen affinity-purified polyclonal anti-KGF antibody (R&D Systems, Minneapolis, Minn.) was added.

Transwell Migration Assay

Migration assays were done using a 24-well transwell migration insert with a polycarbonate filter with 8-μm pores (Millicell; Millipore, Billerica, Mass.). Cells were serum-starved for 24 h and then seeded ($2 \times 10^4$ per upper chamber) and treated with or without recombinant IL-19 protein (concentrations as indicated), and the assays were run for 6 h. Cells that had migrated to the underside of the insert membrane were stained with hematoxylin solution. The cells in the upper side of the insert membrane were rubbed with a cotton swab. The migrated cells on the underside were pictured in a 200× magnification field.

In Vitro Wound Healing Assay

An in vitro "wound healing" assay was used to study alterations in cell motility and migration. Microphotographs were taken at 0 h, 24 h and 48 h, as indicated. The percentage of wound healing was quantitatively analyzed by measuring the distances across the wound (N=20) at the indicated times, and then dividing that by the distance measured at 0 h for each cell line.

Statistical Analysis

All values are expressed as the mean±standard deviation (SD). Statistical analysis was done with GraphPad prism 5.0 (GraphPad Software, San Diego, Calif.) and SigmaPlot 9.0 (Systat Software, Richmond, Calif.). Kruskal-Wallis and Dunn's tests were used. Significance was set at $P<0.05$.

Cutaneous Wound Healing in Diabetic Mice

Animal Model for Diabetic Mellitus

BALB/c mice were from the National Cheng Kung University Laboratory Animal Center and cared for according to the guidelines set up by the National Science Council, Taiwan. The experimental protocol adhered to the rules of the Animal Protection Act of Taiwan and was approved by the Institutional Animal Care and Use Committee of Chi-Mei Medical Center. The mice were housed in a temperature— (25±1° C.) and humidity-controlled (60±5%) room and kept on a 12:12-h light-dark cycle. All cage accessories were sterilized and autoclaved before being placed in the cage. The mice were fed standard laboratory chow and water ad libitum in the Laboratory Animal Center of Chi-Mei Medical Center. The mice were injected intraperitoneally (i.p.) with STZ (200 mg/kg) (Sigma-Aldrich Inc., Saint Louis, Mo., USA) (STZ-diabetic mice) or PBS (PBS-control mice) into fasting mice as described in prior art reference (Woodley D T, O'Keefe E J, Prunieras M. *Cutaneous wound healing: a model for cell-matrix interactions. Journal of the American Academy of Dermatology.* 1985; 12:420-33). Mice were considered to be diabetic if they had elevated plasma glucose concentrations of 350 mg/dL.

Blood Glucose Determination

Blood samples were collected before the treatments and one hour after the last treatment for estimating the levels of plasma glucose, BUN, and creatinine. Blood samples from the mice were centrifuged at 3,000 g for 10 min. Samples were incubated with reagents from glucose kits (AppliedBio assay kits; Hercules, Calif., USA), and the levels of blood glucose were then assessed by an autoanalyzer (Quik-Lab, Ames, Miles Inc., Elkhart, Ind., USA), with samples run in duplicate.

Cutaneous Wound Healing Model

The mice were anesthetized with isoflurane, wiped with 70% ethanol, and shaved. Once the skin was exposed, two full-thickness (including the panniculus carnosus) circular wounds (4 mm in diameter) on each mouse were created using a disposable biopsy punch. Each wound was photographed every day and analyzed using ImageJ software. Mice were topically treated with vehicle or IL-19 (400 ng/mL) twice daily. IL-19 was prepared in an ointment base (vehicle) formulated with 80% Vaseline and 20% liquid paraffin, as described in prior art reference (Martin P. *Wound healing—aiming for perfect skin regeneration. Science.* 1997; 276:75-81). The percentage of wound healing was measured every day for 7 days. There were four groups of mice (n=6 in each group): PBS control mice treated with vehicle; PBS control mice treated with IL-19; STZ-diabetic mice treated with PBS; and STZ-diabetic mice treated with IL-19.

Example 1

Figure 1B:
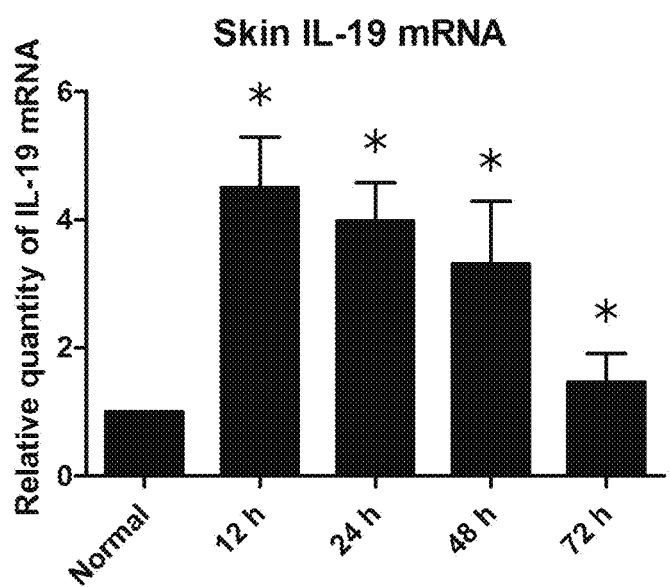
Figure 1C:
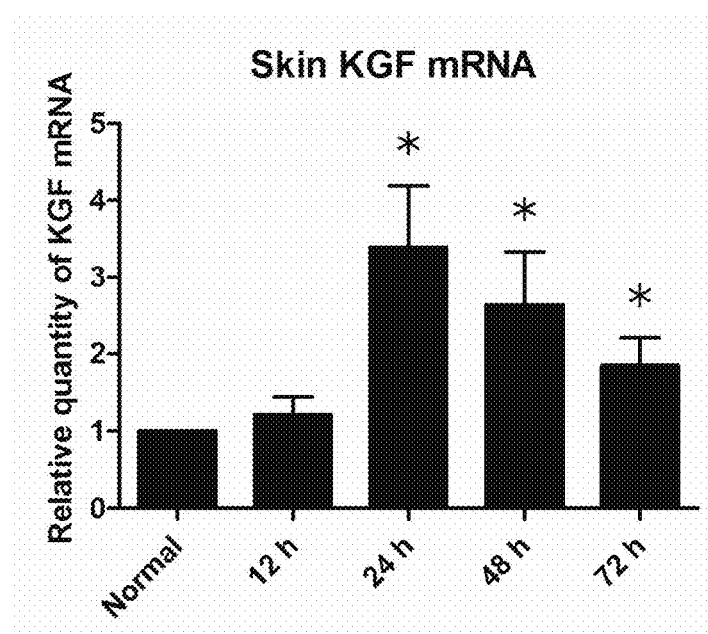
Figure 2A:
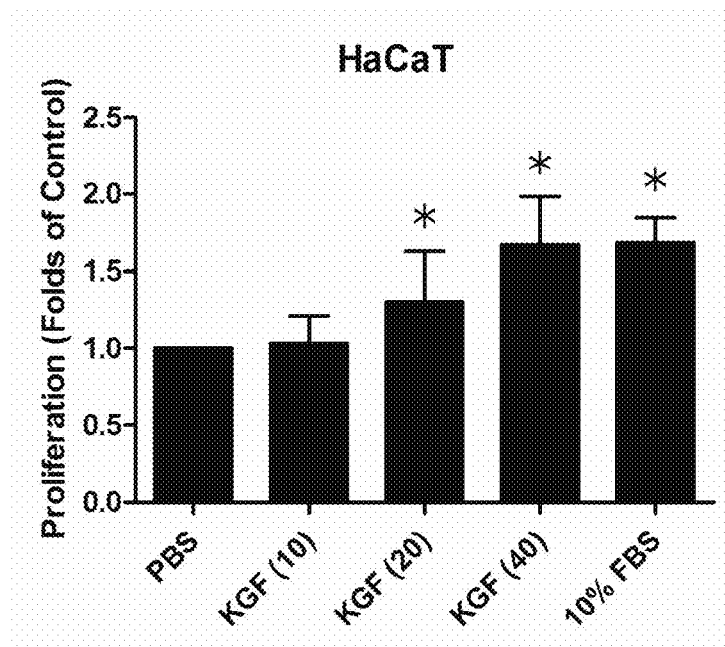
FIGS. 2A and 2B show KGF, but not IL-19, induced keratinocyte proliferation in vitro. We treated HaCaT cells with (A) KGF (10, 20 or 40 ng/mL) or (B) IL-19 (100, 200 or 400 ng/mL) for 24 h, and then used a BrdU incorporation assay to determine cell proliferation. KGF, but not IL-19, induced HaCaT cell proliferation. Data are means±SD, n=6 in each group, *P<0.05.
Figure 2B:
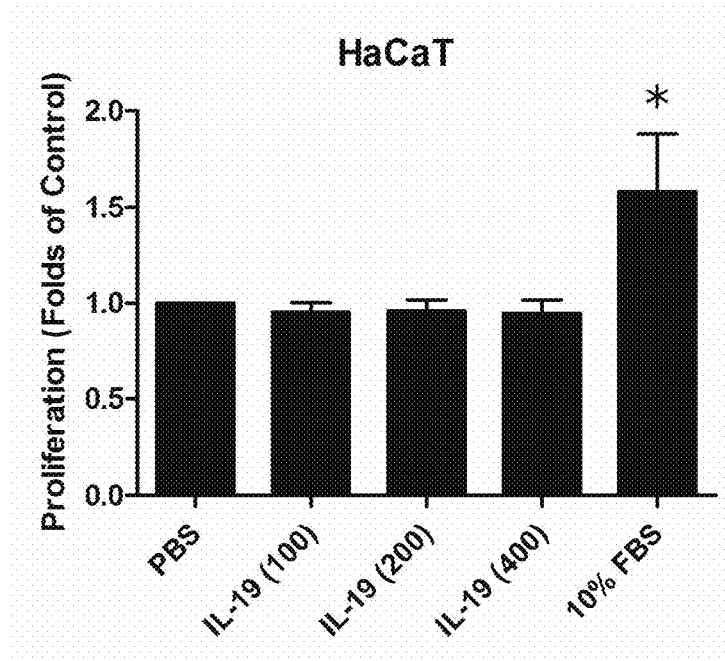

Induction of Keratinocyte Migration by IL-19 IL-19 and KGF were Induced During Skin Wound Healing Using RT-PCR, we first determined the expression of IL-19 and KGF mRNA in mouse skin during wound healing. IL-19 was higher at 12 h, and KGF was higher at 24 h after the skin had been wounded. Both increases in gene expression declined 72 h after the skin had been wounded (FIG. 1). Keratinocyte Proliferation Occurred in KGF-Treated but not IL-19-Treated Cells KGF is pivotal for epithelial cell proliferation during wound healing. We treated HaCaT cells with IL-19 (400 ng/mL) or KGF (40 ng/mL) for 24 h and then determined the cell proliferation using BrdU incorporation assays. Proliferation was significantly higher in KGF-treated (20 ng/mL) HaCaT cells (FIG. 2A) but not affected in IL-19-treated cells (FIG. 2B).

KGF Expression was Induced in IL-19-Treated Fibroblasts and IL-19 Expression was Induced in KGF-Treated Keratinocytes In Vitro To determine whether upregulated IL-19 induces KGF expression in fibroblasts during wound healing, we treated human skin fibroblast CCD966SD cells, which expressed IL-19 receptors IL-20R1/R2 (data not shown), with IL-19 at the indicated concentrations for 12 h and then determined the expression of KGF mRNA and protein using RT-PCR or ELISA as indicated. KGF mRNA and protein were dose-dependently expressed in IL-19-treated fibroblasts (FIGS. 3, A and B, respectively). We also treated human HaCaT cells with KGF. IL-19 mRNA and protein were dose-dependently expressed in KGF-treated HaCaT cells (FIGS. 3, C and D, respectively). These results indicated a cross-amplification of KGF and IL-19 in fibroblasts and keratinocytes.

In Vitro Keratinocyte Migration was Directly Induced in IL-19-Treated Cells

Figure 3A:
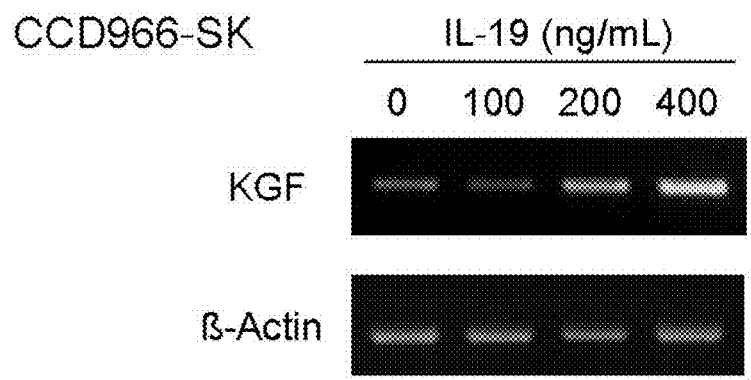
FIGS. 3A-3D show the cross amplification of IL-19 and KGF in keratinocytes and fibroblasts. (A) We treated CCD966SK cells with IL-19 at the indicated concentrations for 12 h and then used RT-PCR to determine the expression of KGF mRNA. Representative data from three independent experiments are shown. (B) We treated CCD966SK cells with IL-19 (100, 200, or 400 ng/mL) or PBS for 24 h and then used ELISA to determine the KGF protein levels in a cultured medium. Data are means±SD, n=6 in each group, *P<0.05. (C) We treated HaCaT cells with KGF at the indicated concentrations for 12 h and then used RT-PCR to determine the expression of IL-19 mRNA. Representative data from three independent experiments are shown. (D) We treated HaCaT cells with KGF (10, 20 or 40 ng/mL) or PBS for 24 h and then used ELISA to determine the IL-19 protein levels in a cultured medium. Data are means±SD, n=6 in each group, *P<0.05.
Figure 3B:
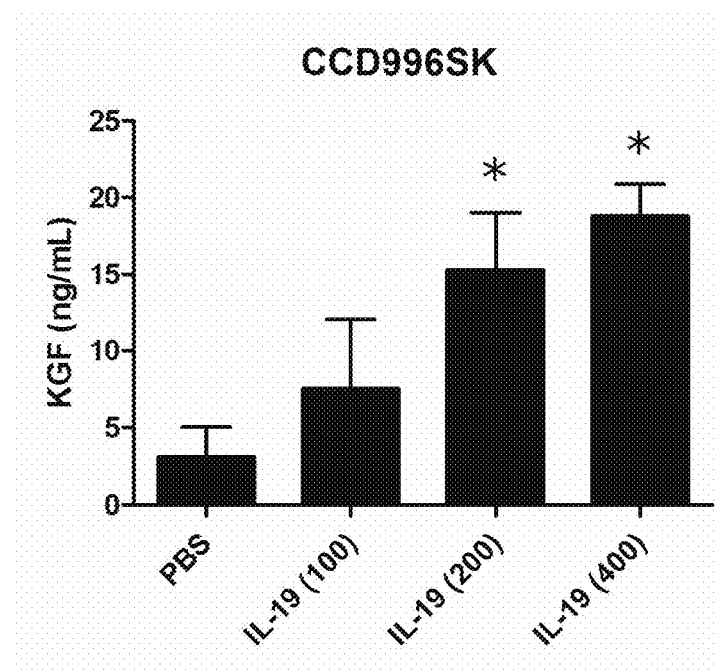
Figure 3C:
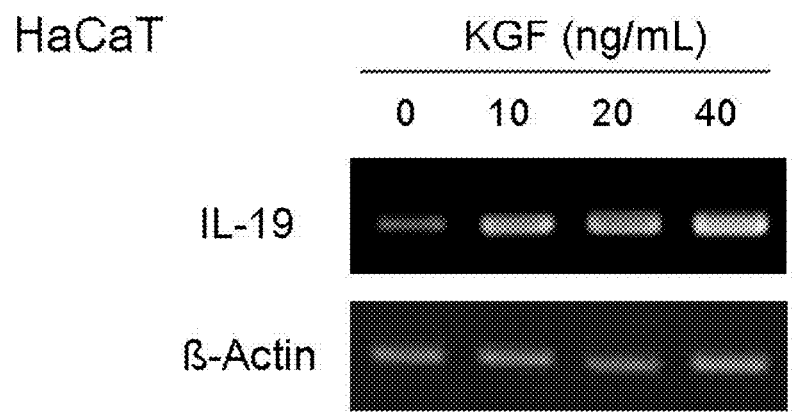
Figure 3D:
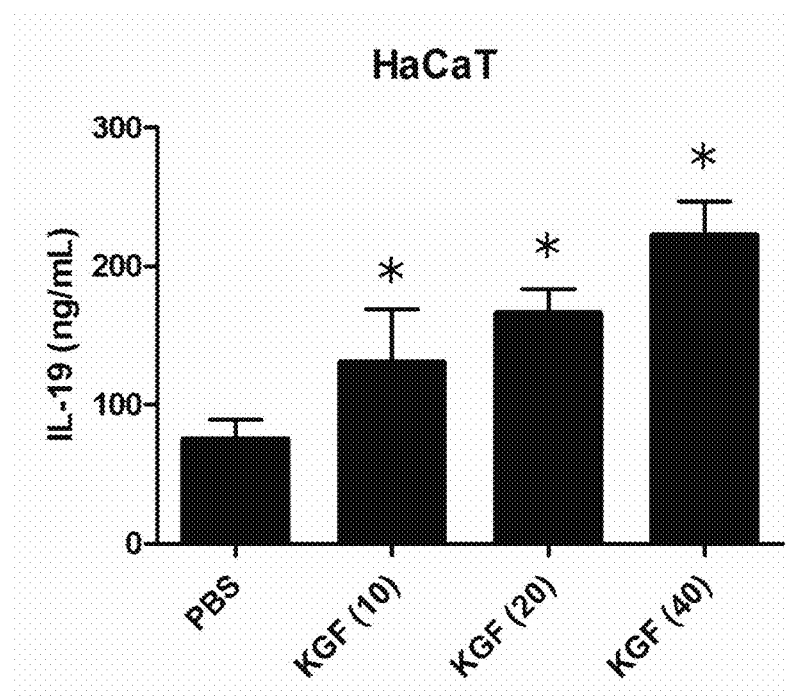
Figure 4A:
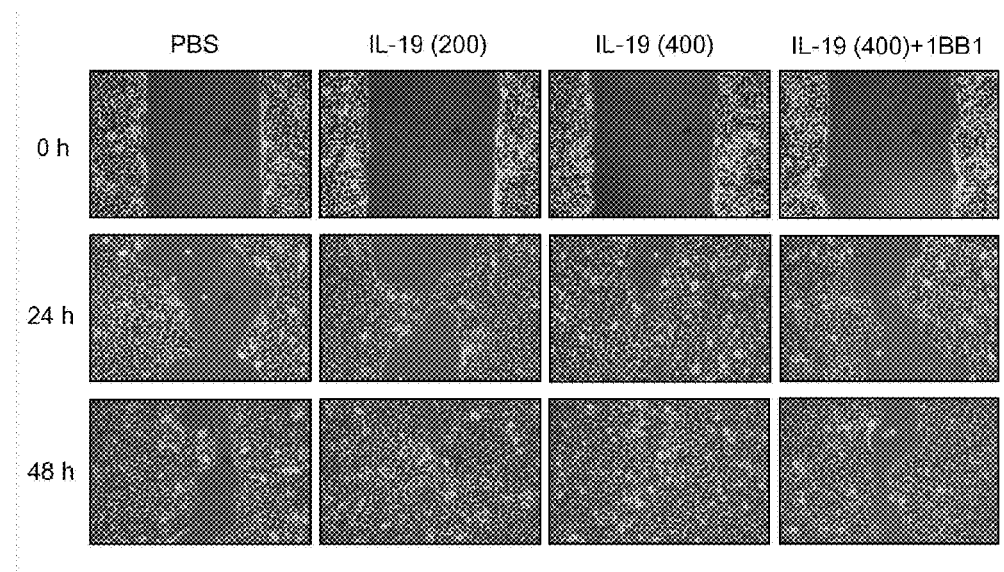
FIGS. 4A and 4B show IL-19 induced migration of keratinocytes in vitro. We determined the migration of HaCaT cells with or without IL-19 (200 or 400 ng/mL) treatment using an (A) scratch healing assay and a (B) transwell assay. 1 BB 1, anti-IL-19 mAb. Representative data from three independent experiments are shown.
Figure 4B:
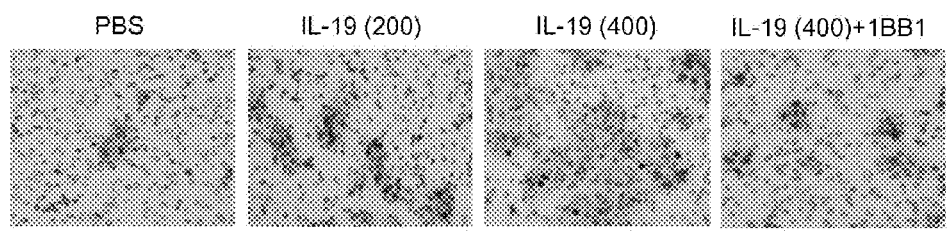
Figure 5A:
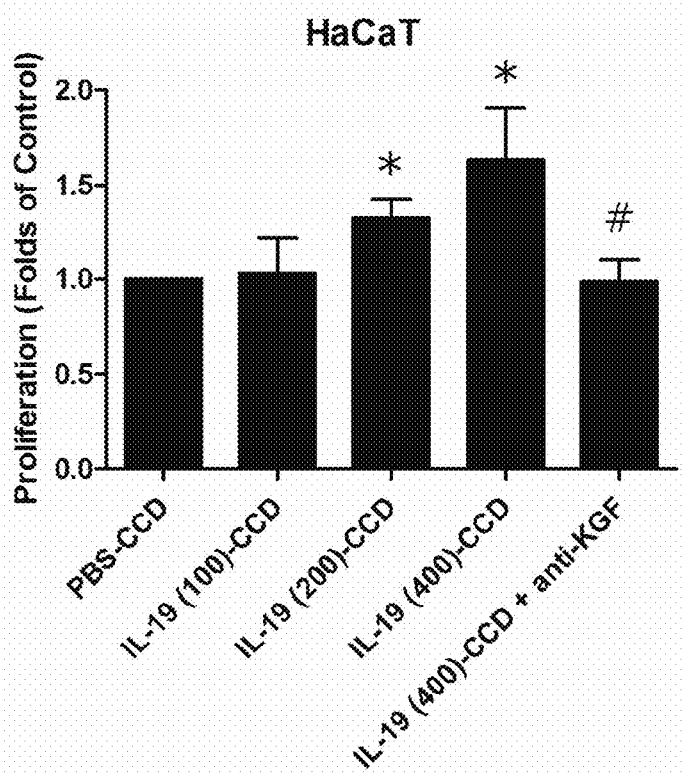
FIGS. 5A-5C show that Cultured media of IL-19- and IL-20-treated fibroblasts promoted proliferation of keratinocytes. (A) We treated CCD966SK cells with IL-19 (100, 200 or 400 ng/mL) or PBS for 24 h and then used the cultured media to treat HaCaT cells for 24 h. Proliferation of the HaCaT cells was determined using a BrdU proliferation assay. Anti-KGF antibody (400 ng/mL) was added to neutralize KGF, as described in Materials and Methods. Data are means±SD, n=6 in each group, *P<0.05 compared with control group, #P<0.05 compared with IL-19 (400 ng/mL) group. (B) We treated CCD966SK cells with IL-20 (100, 200 or 400 ng/mL) or PBS for 24 h and then used ELISA to determine the KGF protein levels in a cultured medium. (C) We treated HaCaT cells with the cultured media of IL-20-treated CCD966SK cells for 24 h. Proliferation of the HaCaT cells was determined using a BrdU proliferation assay. Anti-KGF antibody (400 ng/mL) was added to neutralize KGF, as described in Materials and Methods. Data are means±SD, n=6 in each group, *P<0.05 compared with control group, #P<0.05 compared with IL-20 (400 ng/mL) group.
Figure 5B:
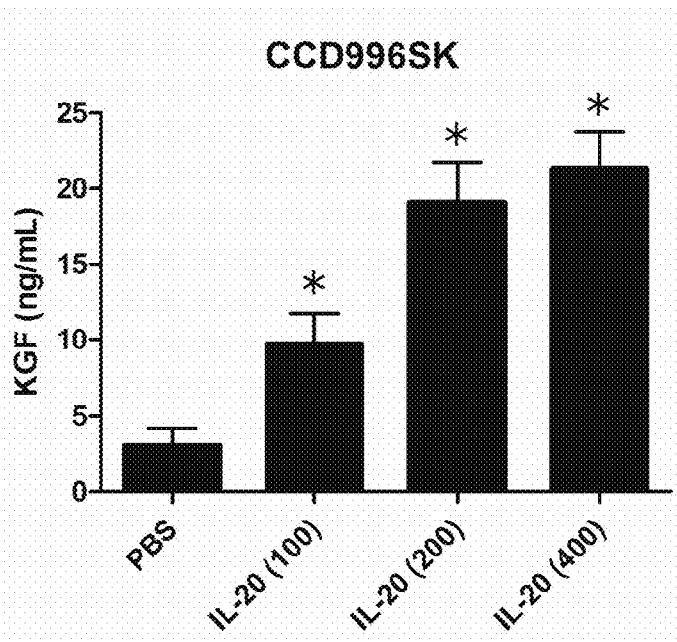
Figure 5C:
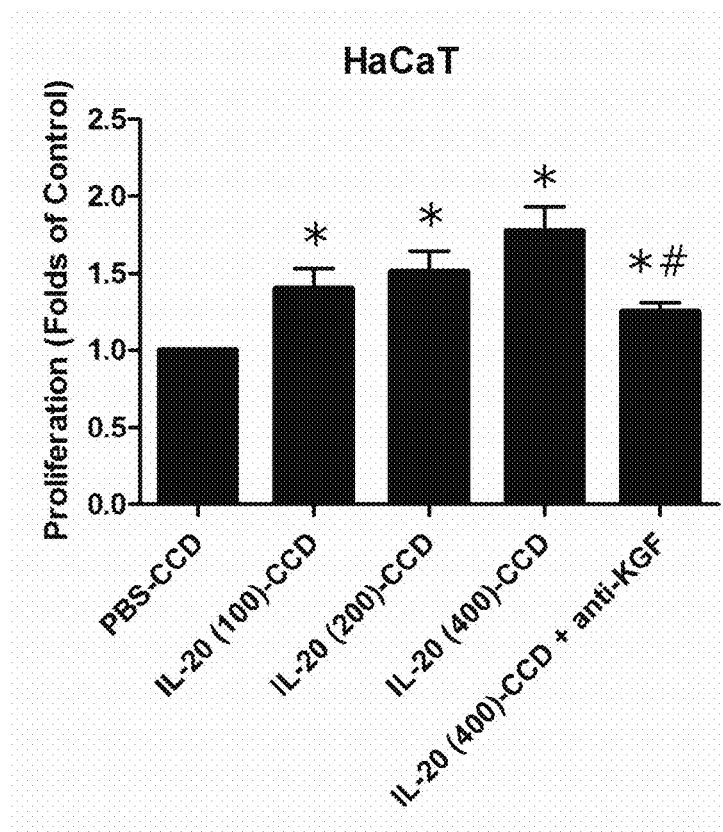

The effect of IL-19 on the migration activity of keratinocytes was determined. HaCaT cells were treated with IL-19 (400 ng/mL) for 6 h and the migration activity was examined using an in vitro wound-healing assay and a transwell migration assay. HaCaT cell migration was promoted in IL-19-treated cells (FIGS. 4, A and B). The migration was inhibited in anti-IL-19 mAb-treated cells, which indicated that the effect of IL-19 on HaCaT cells was specific. Because the proliferation of keratinocytes was not directly induced in IL-19-treated cells, IL-19 may cause keratinocytes to proliferate during wound healing by promoting KGF production in fibroblasts. We had demonstrated that IL-19 induced KGF production in CCD966SD cells (FIG. 3B). We thus treated HaCaT cells with the IL-19-treated media of CCD966SD cells for 24 h. The HaCaT cells treated with the IL-19-treated (200 and 400 ng/mL) media of CCD966SD cells showed significantly more proliferation than the cells treated with the PBS-treated medium of CCD966SD control cells (FIG. 5A). In addition, anti-KGF antibody can inhibit the proliferation. Because IL-19 and IL-20 acts with the similar receptors, we thus determined the effect of IL-20 on KGF production in CCD966SD cells. IL-20 induced KGF production in CCD966SD cells as IL-19 did (FIG. 5B). Moreover, the media of IL-20-treated CCD966SD cells also induced HaCaT cell proliferation which was inhibited by anti-KGF antibody (FIG. 5C).

Wound Healing was Promoted In Vivo in IL-19 and IL-20-Treated Mice

Figure 6A:
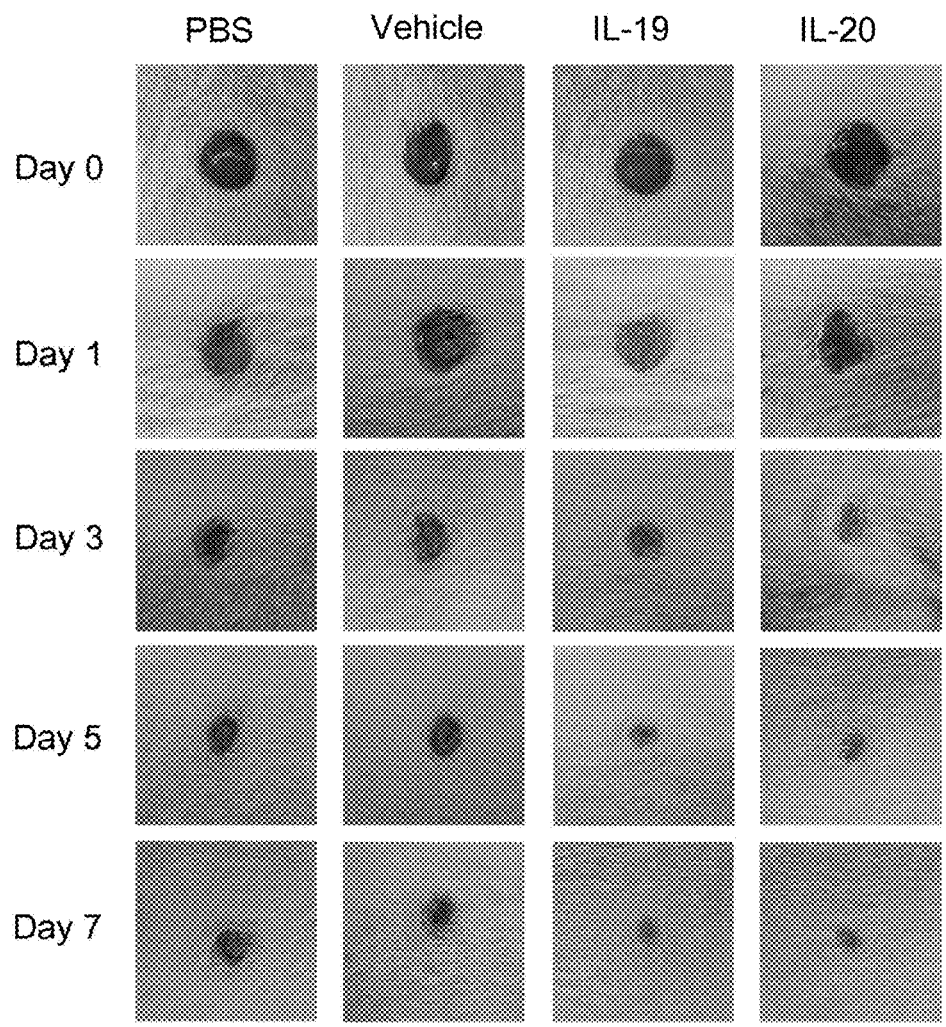
FIGS. 6A and 6B show that IL-19 and IL-20 treatment promoted faster wound healing in vivo. We topically treated mice with 20 µL of IL-19 (400 ng/mL) or IL-20 (400 ng/mL) or PBS or vehicle on the wounded skin every 12 h for 7 days. Representative photos are shown. (A). The wound healing of IL-19- and IL-20-treated mice was significantly faster than that of PBS- and vehicle-treated controls. (B). Data are means±SD, n=6 in each group, *P<0.05.
Figure 6B:
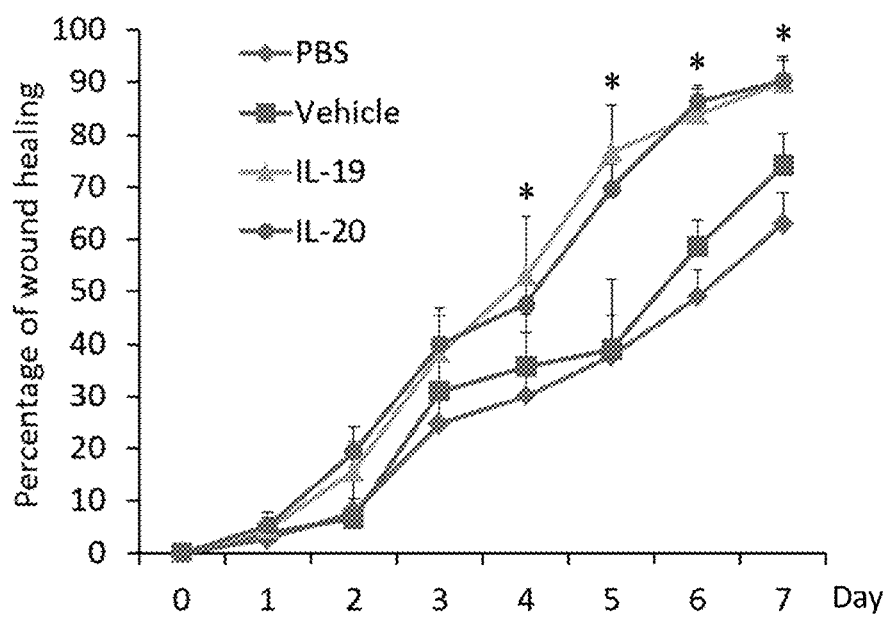

To further investigate the effect of IL-19 on wound healing in vivo, we topically treated the wounded mouse skin with IL-19 or PBS or vehicle control, as described in Materials and Methods. Wound healing was significantly faster in the IL-19-treated group than in the PBS- and vehicle-treated control groups 4 days after the mice had been wounded ($P<0.05$) (FIGS. 6, A and B). We also determined the effect of IL-20 on mouse cutaneous wound healing process. Topically treated IL-20 promoted mice wound healing as IL-19 did (FIGS. 6, A and B).

Example 2

IL-19 Promotes Cutaneous Wound Healing in Diabetic Mice

Figure 7:
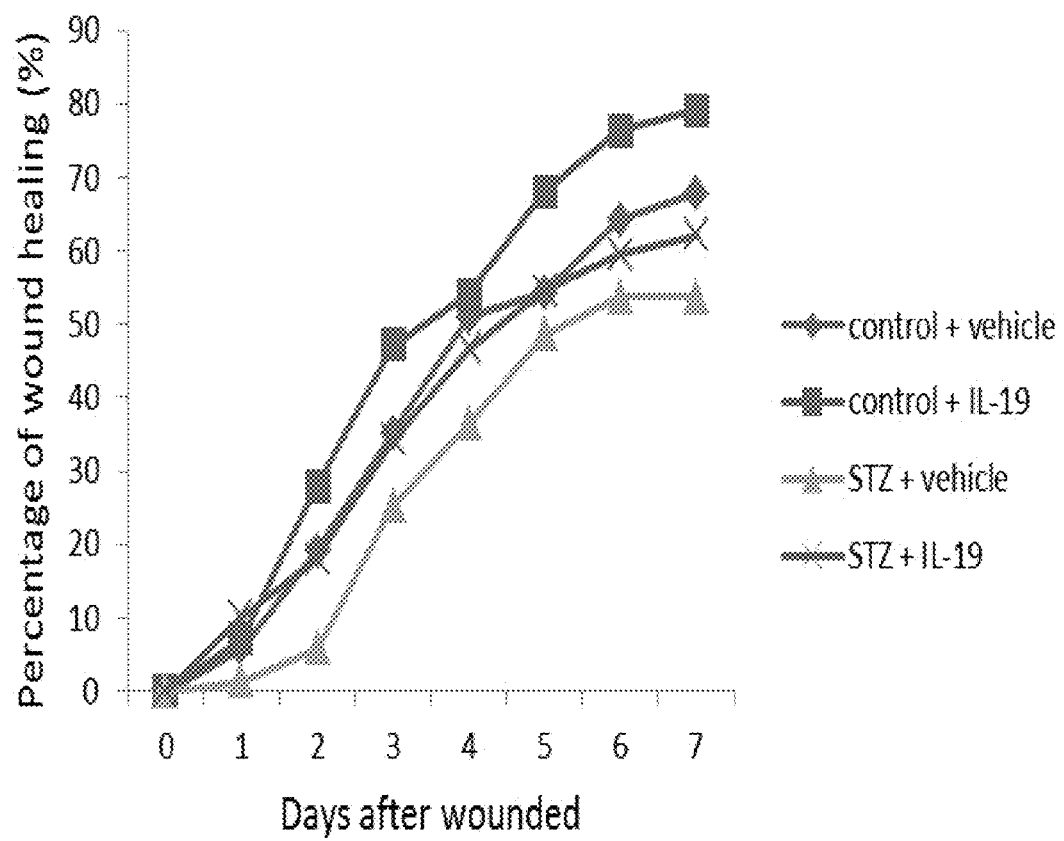
FIG. 7 shows that IL-19 treatment promoted faster diabetes wound healing in vivo.

IL-19 treatment promoted faster wound healing in vivo. We topically treated mice with 20 μL of IL-19 (400 ng/mL) or vehicle on the wounded skin every 12 h for 7 days. The cutaneous wound healing of IL-19-treated PBS-control mice (control+IL-19) was significantly faster than that of vehicle-treated PBS-control mice (control+vehicle). In STZ-diabetes mice, IL-19-treated group (STZ+IL-19) also caused faster cutaneous wound healing than in the vehicle group (STZ+vehicle). Data are means±SD, n=6 in each group, *$P<0.05$ v. vehicle groups (FIG. 7).

What is claimed is:

1. A method for promotion of diabetes wound healing, comprising administering to a fibroblast cell an effective amount of interleukin-19 (IL-19).

2. The method of claim 1, wherein the effective amount of the IL-19 ranges from about 0.001 μg/kg to 5 μg/kg of body weight.

3. The method of claim 1, wherein the IL-19 is for topical or parenteral administration.

* * * * *

```
                        SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Beta-actin Forward Primer

<400> SEQUENCE: 1
gctggaaggt ggacagcgag                                                 20

<210> SEQ ID NO 2
<211> LENGTH: 20
<212> TYPE: DNA
<213> ORGANISM: Artificial Sequence
<220> FEATURE:
<223> OTHER INFORMATION: Beta-actin Reverse Primer

<400> SEQUENCE: 2
tggcatcgtg atggactccg                                                 20

<210> SEQ ID NO 3
<211> LENGTH: 20
<212> TYPE: DNA
<213> ORGANISM: Artificial Sequence
<220> FEATURE:
<223> OTHER INFORMATION: hIL-19 Forward Primer

<400> SEQUENCE: 3
ggcaatgtca ggaacagagg                                                 20

<210> SEQ ID NO 4
<211> LENGTH: 20
<212> TYPE: DNA
<213> ORGANISM: Artificial Sequence
<220> FEATURE:
<223> OTHER INFORMATION: hIL-19 Reverse Primer

<400> SEQUENCE: 4
agcggaataa gacagcctga                                                 20

<210> SEQ ID NO 5
<211> LENGTH: 20
<212> TYPE: DNA
<213> ORGANISM: Artificial Sequence
<220> FEATURE:
<223> OTHER INFORMATION: mIL-19 Forward Primer
```

```
-continued

<400> SEQUENCE: 5
ttccacgaga tcaagagagc                                            20

<210> SEQ ID NO 6
<211> LENGTH: 20
<212> TYPE: DNA
<213> ORGANISM: Artificial Sequence
<220> FEATURE:
<223> OTHER INFORMATION: mIL-19 Reverse Primer

<400> SEQUENCE: 6
cctccagctg attgtagttg                                            20

<210> SEQ ID NO 7
<211> LENGTH: 23
<212> TYPE: DNA
<213> ORGANISM: Artificial Sequence
<220> FEATURE:
<223> OTHER INFORMATION: hKGF Forward Primer

<400> SEQUENCE: 7
aaggctcaag ttgcaccagg cag                                        23

<210> SEQ ID NO 8
<211> LENGTH: 22
<212> TYPE: DNA
<213> ORGANISM: Artificial Sequence
<220> FEATURE:
<223> OTHER INFORMATION: hKGF Reverse Primer

<400> SEQUENCE: 8
gtgtgtcgct cagggctgga ac                                         22

<210> SEQ ID NO 9
<211> LENGTH: 20
<212> TYPE: DNA
<213> ORGANISM: Artificial Sequence
<220> FEATURE:
<223> OTHER INFORMATION: mKGF Forward Primer

<400> SEQUENCE: 9
tgagtccgga gcaaacggct                                            20

<210> SEQ ID NO 10
<211> LENGTH: 22
<212> TYPE: DNA
<213> ORGANISM: Artificial Sequence
<220> FEATURE:
<223> OTHER INFORMATION: mKGF Reverse Primer

<400> SEQUENCE: 10
cctcaggtac cactgggtgc ga                                         22
```